United States Patent [19]
Harris et al.

[11] 4,095,181
[45] June 13, 1978

[54] ROTATING POT SHAPED EDDY CURRENT PROBE IN WHICH ONLY A SMALL FRACTION OF THE LIP FORMING THE OUTER CORE PORTION IS RETAINED

[75] Inventors: Walter Jefferson Harris, Kent; Ronald Murray Neufeld, Seattle, both of Wash.

[73] Assignee: The Boeing Company, Seattle, Wash.

[21] Appl. No.: 751,512

[22] Filed: Dec. 17, 1976

[51] Int. Cl.² ............................................. G01R 33/12
[52] U.S. Cl. ...................................................... 324/238
[58] Field of Search ............ 33/189, 191, 27 D, 27 K, 33/27 E; 356/138, 153, 172; 350/173, 112; 324/37, 40, 34 R

[56] References Cited
U.S. PATENT DOCUMENTS

| | | | |
|---|---|---|---|
| 2,557,029 | 6/1951 | Griffin | 356/172 |
| 3,449,664 | 6/1969 | Smith | 324/40 |
| 3,480,367 | 11/1969 | Husted et al. | 356/138 |
| 3,611,119 | 10/1971 | Madewell et al. | 324/34 R |

FOREIGN PATENT DOCUMENTS

| | | | |
|---|---|---|---|
| 886,247 | 1/1962 | United Kingdom | 324/40 |

*Primary Examiner*—Robert J. Corcoran
*Attorney, Agent, or Firm*—Conrad O. Gardner; B. A. Donahue; Daniel T. Anderson

[57] ABSTRACT

An eddy current probe for detecting cracks in metal skins and adjacent fastener holes which includes first and second coils wound about first and second vertically stacked ferromagnetic core members which members are held in alignment by an associated optically clear shoe member centered by a centering ring, rotation of the shoe within the centering ring permitting inspection of the entire circumference of a fastener hole.

3 Claims, 5 Drawing Figures

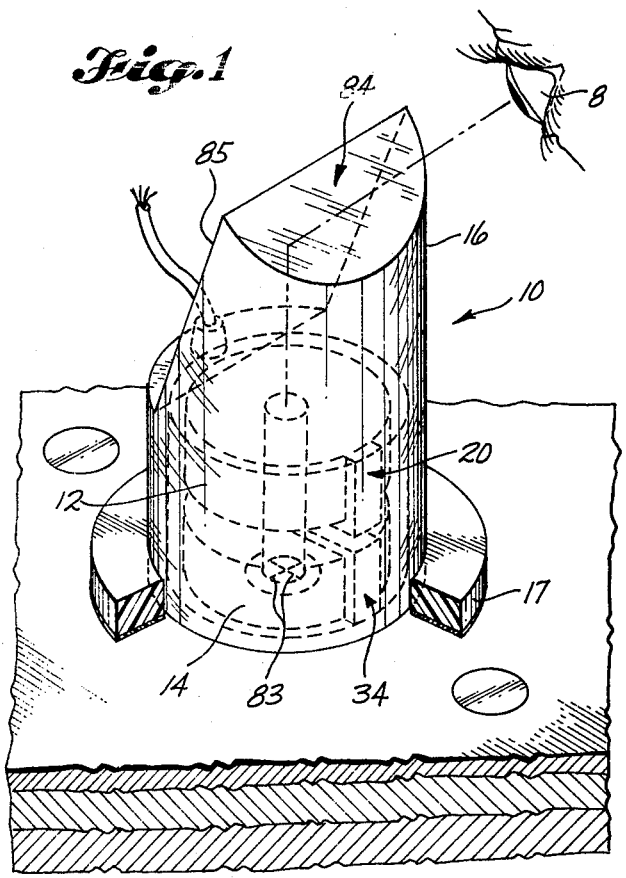
Fig.1
Fig.2
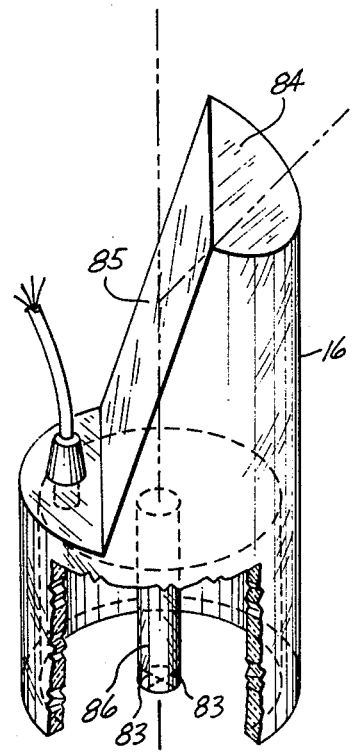
Fig.3
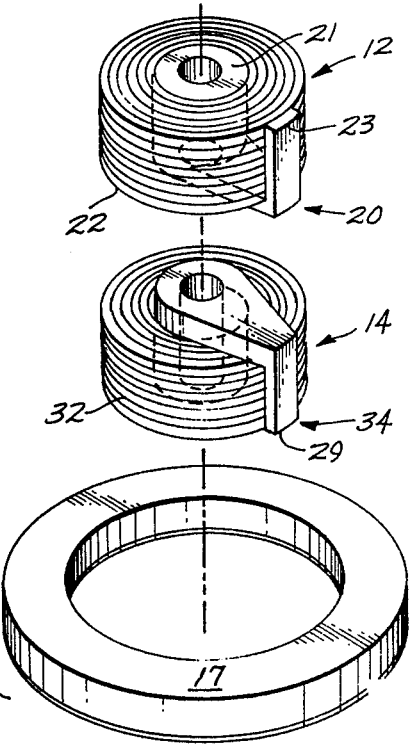

ROTATING POT SHAPED EDDY CURRENT PROBE IN WHICH ONLY A SMALL FRACTION OF THE LIP FORMING THE OUTER CORE PORTION IS RETAINED

This invention relates to eddy current probes for the non-destructive detection of flaws in electrically conductive articles and more particularly to the detection of flaws in the regions of electrically conductive workpiece surrounding fastener holes. The methods and apparatus disclosed represent improvements over those described in our U.S. patent application, Ser. No. 697,815, filed June 21, 1976 entitled "Eddy Current Probe" also assigned to the same assignee as this application.

Heretofore, vertically stacked, multiple coil eddy current crack detecting probe systems have been utilized as exemplified by U.S. Pat. Nos. 2,957,129; 3,378,763; and 3,848,183 wherein the latter patent shows utilization of one of the coils in a three coil system as movable for balancing purposes. U.S. Pat. No. 3,449,664 is illustrative of multiple coil eddy current fastener crack detection apparatus wherein detecting coils rotatably encircle the fastener hole area being tested. In the patent literature it should be further noted that a variable transformer is shown in U.S. Pat. No. 2,585,050 which includes two vertically stacked coils wherein one is rotatable relative to the other, and further that U.S. Pat. No. 2,904,745 is illustrative of a two coil testing system in which means are provided for rotating the unit undergoing test relative to the coils of the testing system. The aforementioned U.S. Pat. No. 3,449,664 and also 3,450,986 show field excitement which is basically uniform but is disturbed where failures exist and a small movable pickup explores the field to find the failures in the structure, and may be contrasted to apparatus exemplary of the present invention wherein the movable element concentrates the field in local areas to increase the resolution, and anomalies among the local distribution indicate failures.

While applicant's earlier referenced copending application Ser. No. 697,815 discloses an eddy current probe structure which surrounds the hole in the workpiece having certain adherent advantages, such stationary encircling probe by nature results in an absolute measurement system wherein fastener length and permeability, and workpiece (aluminum) thickness and conductivity may cause signal noise which interfere with the inspection. In contrast the system of the present invention, instead of comparing instrument responses from fastener to fastener (an absolute measurement system), provides a system which compares the instrument responses around a single fastener (by rotation of probe) thereby reducing the effect of nonrelevant signals produced by changes in fastener length and permeablity and workpiece outer layer thickness and conductivity.

It is accordingly an object of the present invention to provide a system including an optically aligned probe structure having a core assembly rotatable to distinguish cracks and provide system response to cracks detected during rotation of the probe structure.

It is a further object of the present invention to provide an eddy current test probe including means for optically aligning and manually retaining a pair of stacked core members for rotation about a hole in a workpiece.

It is yet another object of this invention to provide probe means having core structure for improving the signal to masking noise ratio in crack detection in low frequency eddy current type non-destructive testing (NDT) systems.

In accordance with the preceding objects, a preferred embodiment of probe structure according to the present invention comprises a two coil system in which the coils and their associated ferrite cores are vertically stacked and held in alignment by an optically clear cylindrically shaped housing which is centered by a circumferentially disposed centering ring. The housing when rotated within the centering ring so as to rotate the enclosed vertically stacked core and coil structures provide inspection of preselected regions around the entire circumference of a fastener hole from a predetermined probe position over the fastener hole.

The aforementioned and other objects and advantages of the invention will become apparent from the following detailed description of an embodiment thereof and the accompanying drawings.

In the drawings

FIG. 1 is a perspective view of an embodiment of the present probe structure showing the optically clear, electrically non-conductive probe housing member for providing optical alignment over a fastener hole;

FIG. 2 is a side view in cross section of the probe structure of FIG. 1 showing magnetic field generated in a fastener and workpiece by the magnetic field generating means of the probe structure;

FIG. 3 is an exploded view in perspective of the probe structure of FIGS. 1 and 2 disassembled;

Figure 4:
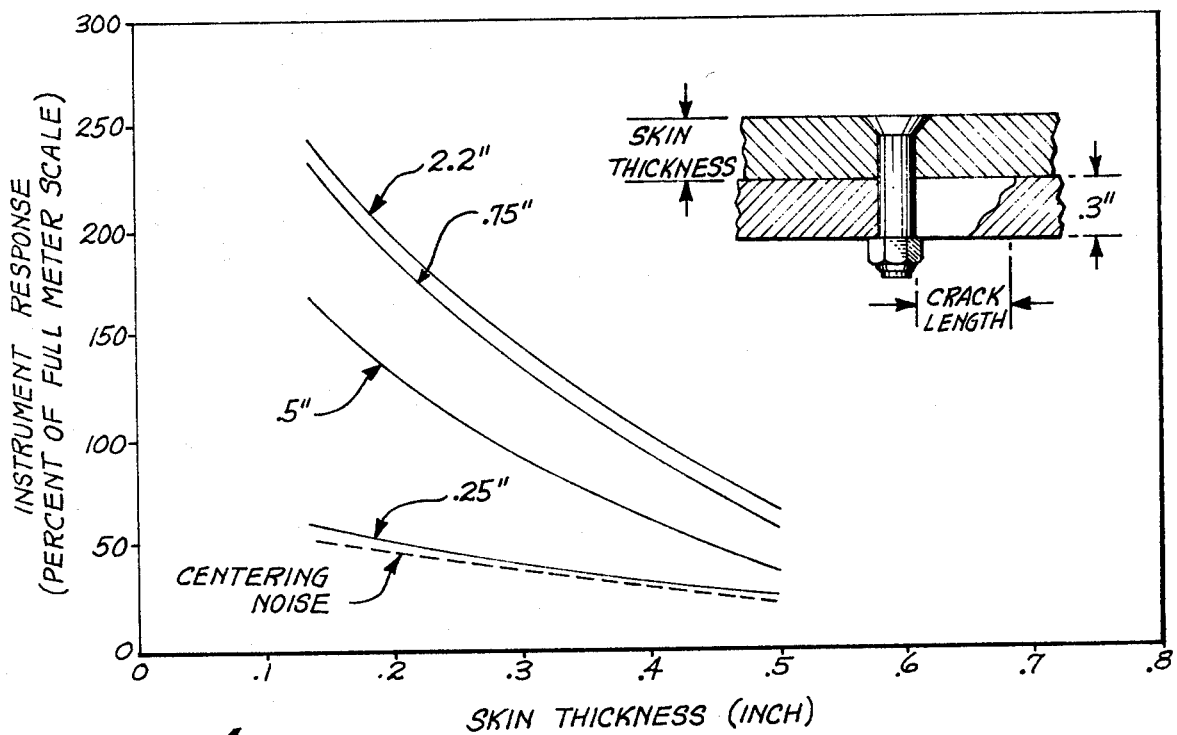
Figure 5:
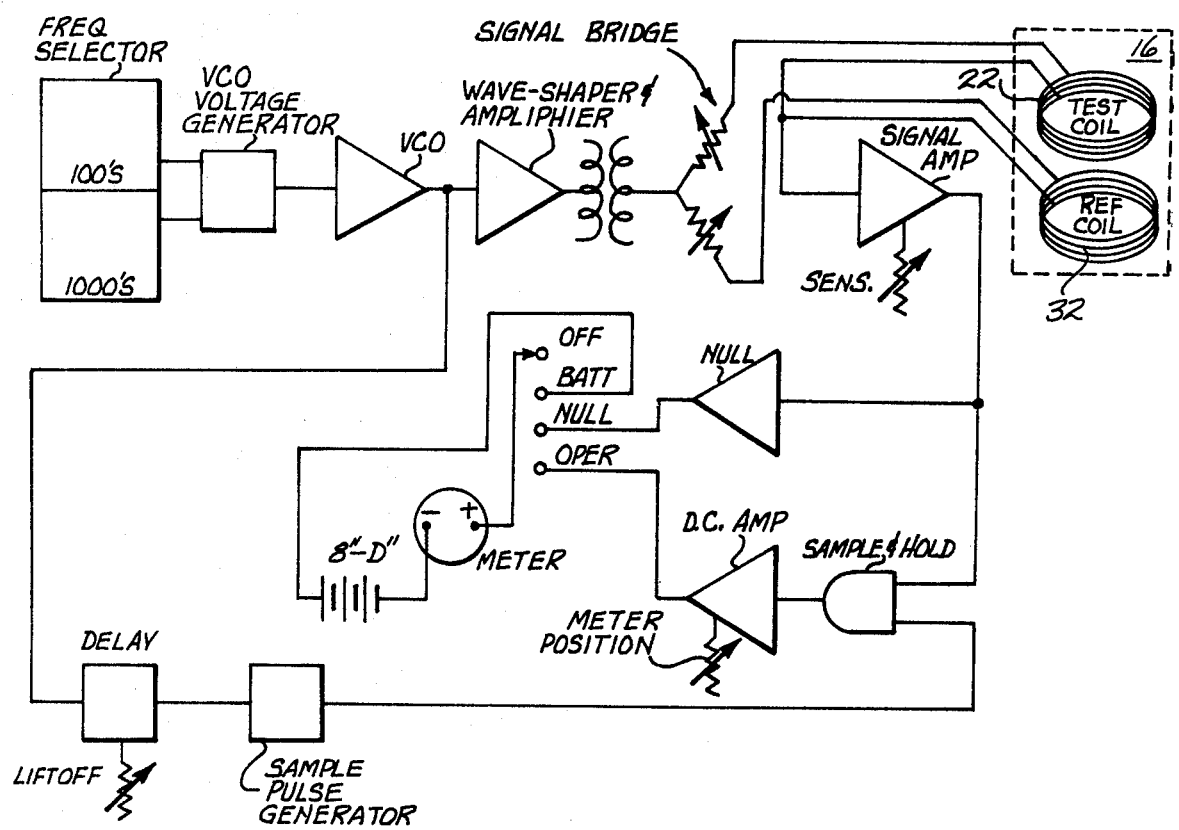

FIG. 4 is a graph illustrative of response of the system of FIG. 5 to simulated cracks versus upper layer thickness of a two layer workpiece joined by a steel fastener shown therein utilizing the probe structure of FIGS. 1 - 3; and, FIG. 5 is a simplified schematic block diagram illustrative of apparatus embodying the probe structure of FIGS. 1 - 3 of the present invention for determining discontinuities in an electrically conductive material.

In order to more readily appreciate the probe structure and system performance of the present invention, reference may be made to FIG. 9 of our earlier referenced copending application Ser. No. 697,815 incorporated herein by reference which shows the crack detection capability of the probe shown therein operated at a frequency of 100 Hz. The probe of the aforementioned application permits inspection of the entire circumference of a fastener hole with one probe position and relies on crack detection by instrument response through comparison of suspect fastener having a crack with one without a crack and thus an absolute measurement system. As a consequence if a horizontal line representative of permeability variations expected in the fasteners to be tested is drawn through the 50 percent instrument response paint (for a positive crack identification) of the aforementioned graph of FIG. 9, it will be observed that 0.25 inch long cracks cannot be easily detected with reliability since the signal level from the permeability variations may exceed the signal from a 0.25 inch crack. The advantages of the present rotating encircling probe shown in FIGS. 1 - 3 may readily be noted by noting in FIG. 4 of this application that the instrument centering noise is below the line representative of a 0.25 inch long crack making detection such detection in their structure possible.

While certain of the advantage of the probe of our aforementioned copending application include: ability to inspect through outer layers up to 0.5 with thick, (2) inspection of the entire circumference of a fastener hole with one probe position and (3) inspection between fasteners with head spacing of only 0.25 inch, the major disadvantage thereof is the absolute measurement system wherein changes in fastener length and permeability and aluminum thickness and conductivity may cause signal noise which interferes with the inspection.

The present probe structure and system provides a low frequency (90 – 700 Hz) eddy current rotating encircling probe which eliminates the disadvantages of the aforementioned stationary encircling probe while retaining the aforementioned recited advantages thereof. Also, the advantages provided by the present probe structure and system hereinafter described include more specifically:

1. Inspection through 0.30 inch thick skins for ½ inch cracks in the second member of the workpiece.
2. Inspection through 0.50 inch skins for large cracks.
3. Inspection of the several individual portions of the entire circumference of a fastener hole by rotation of the probe in one position.
4. Location of the direction of the crack out of the hole.
5. Inspection where fastener spacing is as low as 0.45 inches.
6. Increased signal to noise ratio by reduction of unwanted signals from fastener dimension or composition.
7. Facilitates overhead inspection.

Making reference to the drawings, and now in particular to FIG. 1, it will be noted that eddy current probe 10 includes a reference coil sub-assembly 12 and lower disposed test coil subassembly 14 disposed within electrically non-conductive probe housing member 16 made of an optically clear plastic like material e.g. Lucite, a trade name of the Du Pont Company for a series of polymerized methyl methacrylate thermoplastic resins. It will be further noted, now making reference to FIGS. 2 and 3, that reference coil subassembly 12 comprises a core member 20 made of ferrite having an initial permeability ($u_o$) greater than about 1000 at the magnetic field generating frequency for the system which is less than 1000 Hz viz. 90 to 700 Hz. Ferrite core member 20 in a working embodiment of the invention comprised a manganese-zinc ferrite type 3C8 made by Ferroxcube Company of Saugerties, N.Y. Ferrite core member 20 comprises a cup-shaped pot core structure e.g. type 2616 P-LOO 3c8 also made by Ferroxcube Company in which only about 10% of the lip forming outer core portion 23 of the cup is retained (the rest of the cup bottom and outer lip extending upward therefrom being machined off) so that the amount of ferrite in center cylindrical portion 21 (most readily seen in FIG. 3) is increased relative to the amount of core material retained in outer core portion 23 of pot core structure 20. Circumferentially wound about center cylindrical portion 21 are 1750 turns of number 40 insulated wire which form coil 22. Test coil sub-assembly 14, includes a core member 34 and coil 32, shaped and wound respectively as core member 20 and coil 22 in herein above described reference coil sub-assembly 12.

Test coil sub-assembly 14 is vertically attached back to back with reference coil sub-assembly 12 and coaxially disposed in optically clear cylindrically shaped housing member comprising shoe 16. A centering ring 17 (made of Lucite) coaxially disposed about and retaining eddy current probe 10 (as shown in FIG. 2) coaxially disposed about the central axis 80 of hole 82 permits retention of probe 10 centered over fastener 86 during rotation thereof 360 degrees for inspection for cracks around the periphery of hole 82.

Before continuing with a description of the optical system for first centering probe 10 over fastener 86 before rotation thereof it should be noted (as seen in FIG. 3), that as hereinbefore described only small portions 23 and 29 of the outer lip of pot core members 20 and 34 are retained and now the effect of such reduction of ferrite to small lip portions 23 and 29 on the resultant electromagnetic field can readily be seen in FIG. 2 where it appears (as illustrated by the dotted lines representative of lines of force of such field) that the concentration of the electromagnetic field is much greater where the outer lip ferrite portions 23 and 29 remain.

As a result, when probe 10 is rotated about fastener 86, a greater instrument response is obtained (via the system of FIG. 5 coupled to probe 10) when outer lip portions 23 and 29 are over a crack than when regions where the outer lip portion of the lip have been removed.

This feature of core structure in reference coil subassembly 12 and test coil sub-assembly 14 changes the inspection technique from a system of comparing instrument responses from fastener to fastener to one which compares the instrument response around the periphery of a single fastener thereby reducing the effect of non-relevant signals introduced by changes in fastener length and permeability, and outer layer thickness variation and changes in conductivity.

As hereinbefore noted the present system then permits detection of a 0.25 inch long crack in thin structure possible since not masked by the centering noise (represented by the dotted line in the graph of FIG. 4) which as observed provides less instrument response.

Further crack detection capabilities of rotating encircling probe 10 can be observed from inspection of the graph of FIG. 4 including viz: that 0.5 inch long cracks may be detected through outer layers 0.5 inch thick.

Air gap 92 is provided as can be seen in FIG. 2 between the work surface 94 and the bottom surface of coil 32 by recessing the bottom surface of coil 32 into housing 16 thereby lessening temperature differences and consequent influences and consequent influence of the workpiece upon the two coils 22 and 32, which coils form the bridge arms of a Wheatstone bridge as hereinafter described with respect to the system description in connection with FIG. 5.

Turning now to FIGS. 1 and 2 and a description of the optical path represented by the double dash dotted line for presenting the image of cross hairs 83 to eye 8 of the operator of eddy current probe 10 for centering probe 10 over fastener 86 prior to subsequent rotation thereof within ring shaped centering ring 17 of cylindrical construction for crack detection, it will be noted that cylindrically shaped optically clear housing member 10 has a viewing surface 84 provided as shown in FIG. 2 by cutting off a section of the top of cylindrically shaped housing member 10 at an angle $\theta_1$ of 40° plus or minus 10° with respect to the top surface of the cylinder prior to cutting (as represented by the dotted line to which $\theta_1$ and $\theta_2$ are measured) and a reflecting surface 85 provided by cutting off the remaining portion of the cylinder top at an angle $\theta_2$ of 70° plus or minus 10° with respect to the cylinder top.

Reflective surface 85 is highly polished to reflect the cross hairs 83 to the observers eye 8. Cross hairs 83 comprises a pair of darkened lines at right angles embedded in the bottom surface of and crossing at the center of the bottom surface of housing member 16 provided by a centrally located cylindrically shaped portion 86. Angles $\theta_1$ and $\theta_2$ at which the two flat surfaces 84 and 85 are cut to form the top of cylindrically shaped housing 16 within the ranges hereinbefore mentioned provide transmission surfaces and reflecting surfaces for the field of vision of the observers eye 8 to provide imaging of cross hairs 83 along the double dash dotted line path shown without introducing difficulties into the sighting path shown.

In the method of inspection, then, probe 10 is first centered over fastener 86 by sliding centering ring 17 over the surface of workpiece 94 until cross hairs 83 intersect at the center of the top of fastener 86 and with the system of FIG. 5 energized with probe 10 coupled to the system, probe 10 is slowly rotated within centering ring 17 which is maintained fixed in the selected optically aligned position over fastener 86 until 360 degrees of rotation have been made to determine if instrument response representative of crack detection around the periphery of hole 92 is observed in the system of FIG. 5.

Turning now to the system of FIG. 5, it will be noted that first coil 22 and second coil 32 comprising the test coil and reference coil respectively of the magnetic field sensing and magnetic field generating means respectively form the third and fourth arms of the signal bridge with the first and second variable potentiometers (bridge balance potentiometers) forming the first and second arms. In the system of FIG. 5, the frequency of operation is obtained by the voltage input to the voltage controlled oscillator (VCO). This voltage is generated by the VCO voltage generator circuit. The wave form from the VCO is amplified and shaped then further amplified to a level sufficient to drive the test coils and the bridge circuit. The bridge circuit contains the test and reference coils and the balance potentiometers. The low level signal from the bridge is amplified by the signal amplifier to a level determined by the sensitivity control. This amplified signal is sent to a null detector and also to a sample and hold circuit. The output of the null detector is applied to the meter by the function selector switch in the "null" position. The sample and hold circuit measures the instantaneous voltage of the complex signal waveform for a short interval of time each cycle of the VCO's output voltage. This sampled voltage is stored and is amplified by the direct current amplifier which also amplifies the meter position voltage. The function selector switch in the "operate" position applies this voltage to the meter. The sample circuit receives square wave pulses of the same phase and frequency as the test coil wave form. Each time this square wave goes negative, it triggers a delay oscillator whose output changes states when the first pulse is received and returns to normal some time later, depending on the set point of the lift off control. When the delay oscillator returns to normal this triggers the sample pulse generator and a short, fixed duration pulse is produced. This sample pulse opens the sample and hold gate as long as the sample pulse is present. Rotating the lift off control has the effect of moving out in time the sample pulse with respect to the start of the VCO cycle.

The system is nulled by placing the test probe on a defect free area of the material to be tested and reducing the sensitivity to a value that places the meter below full scale deflection. This reduces the signal to a level that will not saturate the signal amplifier. Next the bridge potentiometer balance controls are rotated causing opposite and nearly equal voltages to be generated in the bridge circuit to "buck" those caused by the "loading"-'effect of the conductive material on the probe. Sensitivity is increased to a level just below amplifier saturation once more and the process is repeated. When maximum sensitivity and minimum meter deflection are obtained the bridge is balanced as closely as possible.

When the function selector switch is in "operate" and the probe is passed over a defect in the material, a change in probe loading occurs due to change in the material's electrical conductivity. This causes a change in the signal voltage wave form. This causes the DC level in the sample and hold circuit to change. This change causes the meter deflection to change indicating a defect in the material under test.

Battery condition is checked by placing the function selection switch in "Batt" position. Meter should read 0.55 Ma or greater. If the meter indicates below 0.55 Ma, battery replacement is necessary. Further details of system of FIG. 5 operation may be seen by review of the maintenance manual for the M1Z8 system of FIG. 5 published and manufactured by Zetec, Inc. of Issaquah, Wash. While an exemplary prior art type system utilizing a bridge circuit is shown in FIG. 5 for the present eddy current probe, it should be noted that other bridge type eddy current systems may be utilized with the present probe, e.g. Nortec Company of Richland, Wash. Utilizing the present probe in the system of FIG. 5, with the probe positioned on fasteners in holes with simulated cracks, instrument of FIG. 5 response for each simulated crack under different workpiece (aluminum aircraft skin) thicknesses yielded the results shown in FIG. 4.

Based on the instrument gain settings used for present purposes, a crack is considered detectable when the instrument response from a crack exceeds 50% of full scale.

As a result of the preceding, it should be noted that the presented probe which provides third and fourth arms of a bridge in a system such as shown in FIG. 5, when utilized at the hereinbefore mentioned low frequencies can be utilized instead of expensive radiographic inspections and inspections of the type requiring fastener removal resulting in inspection cost savings and reduced aircraft down time.

What is claimed is:

1. The method of nondestructively testing an electrically conductive material having an exterior surface and a hole formed therein which opens at the surface and has a fastener disposed therein, the method consisting of:
   positioning an eddy current probe including a pot core in which only about 10% of the lip forming the outer core portion is retained and 34 having a center cylindrical portion 21 within a centering ring with said eddy current probe and centering ring abutting said exterior surface;
   sighting through an optical system disposed in said eddy current probe and passing through said center cylindrical portion 21 while sliding said eddy current probe disposed in said centering ring across said exterior surface to coaxially align said center cylindrical portion 21 of said eddy current probe with the hole and fastener; and rotating the outer lip portion 29 of said eddy current probe through 360° or over a crack until the crack is detected while retaining said centering ring at the position on said exterior surface providing coaxial alignment of said center cylindrical portion 21 of said eddy current probe with the hole and fastener.

2. An eddy current probe for inspecting a workpiece having a hole formed therein and having a fastener disposed therein for defects, said probe including the combination of:

a first ferromagnetic pot core member in which only a small fraction of the lip forming the outer core portion is retained and 20 having a center cylindrical portion 21;

a second ferromagnetic pot core member in which only a small fraction of the lip forming the outer core portion is retained and 34 having a center cylindrical portion 21;

a first winding 22 circumferentially wound about said center cylindrical portion 21 of said first ferromagnetic pot core member 20;

a second winding (32) circumferentially wound about said center cylindrical portion 21 of said second ferromagnetic pot core member 34;

a cylindrically shaped optically clear probe housing 16 for maintaining said center cylindrical portions 21 in coaxial alignment;

said cylindrically shaped optically clear probe housing 16 having a portion of the top section angularly cut forming a flat viewing surface 84 and remaining top section cut off at a cooperating angle to that of the viewing surface forming a reflecting surface 85, and said cylindrically shaped optically clear probe housing having an inner centrally located cylindrically shaped portion 86 extending through said center cylindrical portions 21 of said first and second pot core members 20, 34, said inner centrally located cylindrically shaped portion 86 having cross hairs 93 embedded in and crossing at the center bottom surface thereof so that said reflective surface provides reflection of cross hairs 83 to the eye of the operator viewing the centering of probe 10 over said fastener 86 through viewing surface 84; and means permitting rotation of said outer lip portions through 360° once the latter is centered over said fastener.

3. The eddy current probe of claim 2 wherein said first flat viewing surface 84 is inclined in a plane 40° plus or minus 10° with respect to a plane parallel to said center bottom surface and said second flat surface is inclined in a plane 70° plus or minus 10° with respect to a plane parallel to said bottom surface.

* * * * *